(12) United States Patent
Zambonino et al.

(10) Patent No.: US 7,288,280 B1
(45) Date of Patent: Oct. 30, 2007

(54) COMPLETE FEED FOR FISH LARVAE AND METHOD FOR PREPARING SAME

(75) Inventors: José Zambonino, Loc Maria Plouzane (FR); Chantal Cahu, Brest (FR); Patrick Quazuguel, Loc Maria Plouzane (FR); Pierre Bergot, Ustaritz (FR)

(73) Assignees: Institut National de la Recherche Agronomique (INRA), Paris (FR); Institut Francais de Recherche pour l'Exploitation de la Mer (IFREMER), Issy les Moulineaux (FR)

( * ) Notice: Subject to any disclaimer, the term of this patent is extended or adjusted under 35 U.S.C. 154(b) by 0 days.

(21) Appl. No.: 09/959,312

(22) PCT Filed: Apr. 21, 2000

(86) PCT No.: PCT/FR00/01068

§ 371 (c)(1),
(2), (4) Date: Aug. 18, 2003

(87) PCT Pub. No.: WO00/64273

PCT Pub. Date: Nov. 2, 2000

(30) Foreign Application Priority Data

Apr. 21, 1999 (FR) .................................. 99 05049

(51) Int. Cl.
A23K 1/18 (2006.01)
A23J 3/00 (2006.01)

(52) U.S. Cl. .................. 426/656; 426/2; 426/643; 426/601; 426/805

(58) Field of Classification Search .................. 426/2, 426/656, 601, 643, 805, 658, 807
See application file for complete search history.

(56) References Cited

U.S. PATENT DOCUMENTS 4,798,727 A * 1/1989 Miller ..................... 426/69
4,826,691 A * 5/1989 Prochnow ................ 426/1
4,971,820 A * 11/1990 Likuski et al. .......... 426/281
5,661,981 A 9/1997 Laux et al.
6,168,815 B1 * 1/2001 Kossmann et al. ...... 426/302
6,299,928 B1 * 10/2001 Takeuchi et al. ........ 426/656
6,623,776 B1 * 9/2003 Wathne et al. .......... 426/385
6,812,009 B2 * 11/2004 Gladue et al. .......... 435/134

FOREIGN PATENT DOCUMENTS

| EP | 0 292 052 | | 11/1988 |
| GB | 1 318 463 | | 5/1973 |
| JP | 58 047447 A | | 3/1983 |
| JP | 58047445 | * | 3/1983 |
| JP | 60262579 | * | 12/1985 |
| JP | 61037055 | * | 2/1986 |
| JP | 03 007546 A | | 1/1991 |
| JP | 03007546 | * | 1/1991 |
| JP | 09037723 | * | 2/1997 |
| RU | 2054254 | * | 2/1996 |
| WO | 92/16115 | | 10/1992 |
| WO | 97/42836 | | 11/1997 |

OTHER PUBLICATIONS

Cahu et al., 1999, Aquaculture, vol. 171, pp. 109-119 (cited in specification).*
John Sargent et al., "Lipid Nutrition of Marine Fish During Early Development: Current Status and Future Directions," *Aquaculture*, V. 179, 1999 pp. 217-229.
C. Cahu et al., "Preliminary Results on Sea Bass (*Dicentrarchus labrax*) Larvae Rearing with Compound Diet from First Feeding. Comparison with Carp (*Cyprinus carpio*) Larvae," *Aquaculture*, V. 169, 1998, pp. 1-7.

* cited by examiner

*Primary Examiner*—C. Sayala
(74) *Attorney, Agent, or Firm*—Young & Thompson

(57) ABSTRACT

The invention concerns a complete feed composition for fish larvae, characterized in that it has a phospholipid content not less than 8.5 wt. % of dry matter of the feed.

20 Claims, 2 Drawing Sheets

COMPLETE FEED FOR FISH LARVAE AND METHOD FOR PREPARING SAME

Figure 1:
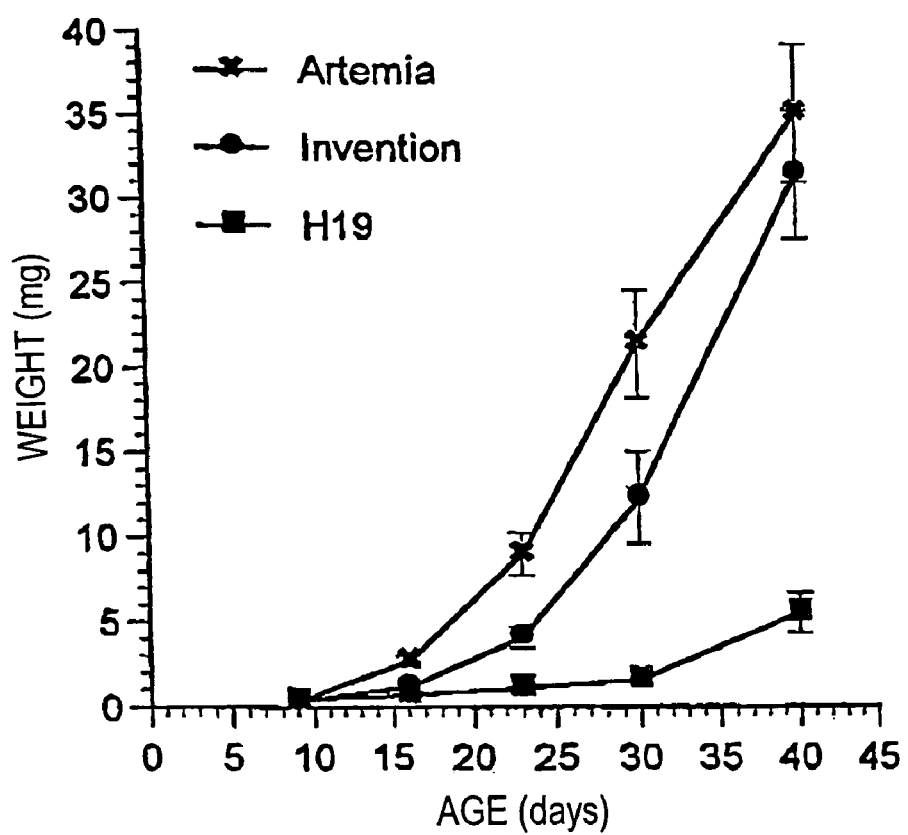

The present invention relates to a complete feed composition for fish larvae, as well as a method for preparing same.

The production of fish alevins, and more particularly of sea fishes, involves nowadays necessarily a feeding stage using living prey, such as Rotifera and *Artemia*.

The period of time that living prey is used during an alevin production cycle in a hatchery depends on the sea fish species. This period of time generally varies from 40 to 50 days and can reach as much as about 60 days for the fish species grown in Europe.

Using a substitute feed for living prey, a so-called weaning feed, only occurs subsequently, gradually and generally more than 40 days after hatching.

Using living prey, and more particularly *Artemia*, in the alevin feeding within hatcheries involves numerous inconvenients.

The need to use a secondary breeding structure in order to produce the living prey adapted for feeding alevins represents a first inconvenient, both industrial and economical.

Secondly, the living prey quality and the living prey supply opportunities are uncertain and quite variable from one year to another. Needless to say that the living prey quality has direct consequences on the survival and growth level of alevins which are fed using the latter.

It has thus been discovered that using a substitute feed for living prey could offer numerous advantages, namely because it is more easily preserved and stored, the quality of the alevin feed supply is highly reproducible and, consequently, the quantitative and qualitative results are more regular upon breeding fish larvae.

Some attempts to produce feed compositions used as partial or total substitutes for living prey have been disclosed in the state of the art.

French patent application no. 2 572 625 discloses a feed composition for fish larvae adapted to be partially substituted for living prey. It comprises dried yolk powder mixed with a liquid lipid at room temperature.

Other feed substitutes are disclosed in a first article by CAHU et al. (1998, Aquaculture, vol. 169, pages 1-7), comparing three feed substitutes from the standpoint of their ability to ensure the survival and growth of two fish types: bass and carp.

The results show that the substitute composition having the best properties as far as the survival and growth level of the alevins is concerned has a protein content comprising, in equal parts, powdered yeast (Protibel) and a fish protein hydrolyzate (respectively 40% by weight of the composition dry matter), soya lecithin in an amount of 5% by weight of the dry matter and a lipid content in the form of 2% by weight of fish oil.

This article' authors alleged that although the feed substitute concerned is the best amongst the three substitutes being tested, its nutritional properties are not satisfactory enough to contemplate using it as a substitute for living prey.

Another article by CAHU et al. (1999, Aquaculture, vol. 171, pages 109-119) describes four feed substitutes for alevins, respectively called H0, H19, H338 and H58.

The authors suggest to supply part of the proteins not only in the form of fish meal, but also in the form of a fish protein hydrolyzate preparation, in an amount of 19%, 38,5% and 58% by weight of dry matter, respectively, of the H19, H38 and H58 substitutes.

These feed substitutes have been exclusively tested on bass larvae which have been fed with any of these four compositions as early as the fifth day following the mouth opening (day 10 counted as from the hatching day).

The experiment results show that the H19 preparation has the best nutritional qualities, not only from larvae survival percentage standpoint but also from their growth and quality standpoint (bone malformation rate and larvae maturity). The H19 substitute composition particularly comprises, expressed in percent by weight of dry matter, 58% of fish meal, 19% of fish soluble protein concentrate, 5% of soya lecithin, 4% of fish oil, 8% of a vitamin additive as well as 5% of a mineral additive.

This article has shown that the optimum content of fish protein soluble concentrate, the only variable parameter of the various feed substitute compositions tested in this article, was 19%. The authors have concluded that incorporating the fish protein hydrolyzate in such an accurate proportion is able to increase the larvae quality, evaluated observing the skeleton malformation rate.

It has now been discovered according to the invention that the phospholipid content of compositions adapted for feeding fish larvae, more particularly sea fishes, is an essential feature as far as the nutritional qualities of such compositions are concerned and more particularly regarding their ability to maintain a high survival rate in fish larvae, to ensure these larvae a high growth rate, and to make it possible to obtain an excellent quality alevin population, with a specially low skeleton malformation rate and a high degree of physiological maturity.

The object of the invention is to offer a complete mixed feed composition for fish larvae, characterized in that it has a phospholipid content at least equal to 8.5% by weight of the dry matter of said composition.

According to the invention, it has been shown that a higher phospholipid supply than in the compositions of the state of the art is essential to produce a complete feed resulting in survival and growth rates of larvae equal as or higher than those obtained with living prey such as Rotifera and *Artemia*. The phospholipids are present in the egg yolk being used by the fish embryo for its growth until it is able to ingest exogenous feed. They are also present in living prey. The phospholipids should also be supplied in a sufficient amount in the complete feed for fish larvae whereas such a supply is not necessary in feed for adult fishes.

The phospholipid content of the complete feed according to the invention ranges between 8.5 and 25% by weight of the feed dry matter, preferably between 10 and 20%.

According to an aspect of the invention, a final total phospholipid content in the feed higher than 8.5% is guaranteed by adding at least 6% of phospholipids from vegetal origin, which are added to the phospholipids possibly supplied by the other ingredients.

Lecithins from vegetal origin can be used, such as soya lecithin, or lecithin from other oleaginous plants such as sun-flower or colza.

It is meant by term "lecithin" lipid blends in which the phospholipids represent more than 50% of the total lipids. The most common phospholipid classes present in lecithins are phosphatidylcholine, phosphatidylethanolamine and phosphatidylinositol. Commercial lecithins can exhibit a variable phospholipid content, including in a de-oiled form (about 90% of phospholipids) or not de-oiled (about 50% of phospholipids). Thus, adding 6% of phospholipids can be done not only by adding 7% of lecithin to 90% of phospholipids but also by adding 12% of lecithin to 50% of phospholipids.

The vegetal lecithins contain $C_{18}$ fatty acids from n-3 and n-6 essential fatty acid series (linoleic acid: 18:2n-6 and linoleic acid: 18:3n-3), but are free from $C_{20}$ and $C_{22}$ polyunsaturated fatty acids, including arachidonic acid (20:4n-6), eicosapentaenoic acid (EPA, 20:5n-3) and docosahexaenoic acid (DHA, 22:6n-3). This does not limit the use of lecithins as the latter fatty acids can be supplied, separately from added lecithins, by feed other ingredients. This latter supply can be in the form of triglycerides or phospholipids, using in particular products from fishes, such as fish oils or fish meals. The complete feed composition of the invention contains a neutral lipid supply, originating from fish meal and containing polyunsaturated long fatty acids, in particular of the (n-3) series. The (n-3) series fatty acids represent 2.5% by weight of the dry matter in feed according to the invention. Due to such possible complementary supply in fatty acids, the fatty acid composition of lecithins is not critical and modified lecithins such as hydrogenated lecithins can also be used.

According to another aspect of the invention, the total lipid content of the feed is higher than 25% by weight of the dry matter. The presence of a sufficient amount of phospholipids in the feed, on top of its specific interest, improves the digestive use of the other lipid components of the feed and, more particularly, that of the neutral lipids and in particular that of the triglycerides. One of the advantages resulting from increasing the feed lipid content is to increase the digestible energy content to meet the larvae energetic needs.

It has been shown according to the invention that a feed composition containing, according to one aspect of the invention, 17% non de-oiled soya lecithin (% of the feed dry matter) and having a total phospholipid content of 12% (corresponding to about 9% originating from the lecithin and 3% originating from the other feed ingredients) would ensure survival and growth rates much higher than those obtained in the state of the art with the above-mentioned H19 substitute.

Moreover, it has been shown that the survival and growth results obtained with a feed according to the invention are equal to or higher than those obtained with living prey, i.e. with Rotifera during the first feeding days and with *Artemia* the following days.

According to further aspect, the non hydrolysed fish protein content of the complete feed composition according to the invention is higher than 50% by weight of the dry matter.

The non hydrolyzed protein supply preferably comprises fish meal which is part of the complete feed composition, in an amount ranging between 45 and 60% by weight of the dry matter, more preferably about 56% by weight of the dry matter.

According to another aspect of the invention, the complete feed composition additionally has a hydrolyzed protein content, preferably in the form of a fish soluble protein concentrate, ranging between 8 and 25%, more preferably between 10 and 22% and most preferably about 14% by weight of the composition dry matter.

Advantageously, a composition for preparing a complete feed for fish larvae according to the invention will additionally comprise a vitamin additive.

A vitamin blend can be prepared for example having the following vitamin composition, expressed in kilograms of the vitamin blend:

retinol acetate (1 g)
cholecalciferol (2.5 mg)
all-rac-α-tocopherol acetate (10 g)
menadione (1 g)
thiamine (1 g)
riboflavine (0.4 g)
D-calcium pentothenate
pyridoxine HCl (0.3 g)
cyanocobalamine (1 g)
niacin (1 g)
choline chloride (200 g)
ascorbic acid (20 g)
folic acid (0.1 g)
biotin (1 g), and
meso-inositol (30 g).

The complete feed composition for fish larvae according to the invention may additionally comprise a mineral additive.

Preferably, such a mineral additive is made of a mineral blend having the following formulation, expressed in kilograms of mineral blend:

KCl (90 g); KI (40 mg); $CaHPO_4.2H_2O$ (500 g); NaCl (40 g); $CuSO_4 5H_2O$ (3 g); $ZnSO_4.7H_2O$ (4 g); $CoSO_47H_2O$ (20 mg); $FeSO_4.7H_2O$ (20 g); $MnSO_4.H_2O$ (3 g); $CaCO_3$ (215 g); $MgSO_4.7H_2O$ (124 g) and NaF (1 g).

The vitamin and mineral compound supply of the complete feed composition according to the invention may be qualitatively and quantitatively adapted depending on the final vitamin and mineral contents resulting from the supply of the other raw materials used in preparing such a composition, for example the vitamin and mineral content from the protein, lipid and phospholipid sources.

Advantageously, the complete feed composition according to the invention may also contain small quantities of appetizing factors, such as betaine.

Preferably, such appetizing factors are used in compositions according to the invention in the order of 0.5 to 3% by weight of the dry matter, for example, in the order of about 1% by weight of dry matter.

Additionally, the water final content of the complete feed composition for fish larvae according to the invention is not higher than 14% by weight of the composition, and is preferably in a range from 7 to 10% by weight and most preferably about 8% by weight of the final composition.

Most preferably, a complete feed composition according to the invention will have the following formulation, expressed in weight of dry matter:

TABLE I

| Ingredients | % of dry matter |
| --- | --- |
| Fish meal | 56 |
| Fish soluble protein concentrate | 14 |
| Soya lecithin | 17 |
| Vitamin blend | 8 |
| Mineral blend | 4 |
| Betaine | 1 |

According to another aspect of the invention, such a composition will have the following formulation, expressed in weight of dry matter:

| | |
| --- | --- |
| Total proteins (N × 6.25): | 56% |
| Total phospholipids: | 12% |
| Total lipids: | 26% |
| Ashes: | 14% |

The complete feed composition for fish larvae according to the invention may advantageously be used for preparing a complete mixed feed for feeding fish larvae in the form of granules having a defined grain size.

Preferably, the size of complete mixed feed granules is such that the biggest size is lower than 600 μm. The granule size may be adjusted in order to prepare a complete mixed feed appropriate for differently old fish larvae or also for fish larvae from species with different sizes.

Consequently, according to a first embodiment of the complete mixed feed for fish larvae according to the invention, the granule size ranges from 400 to 600 μm.

According to a second aspect of the complete mixed feed according to the invention, the granule size ranges between 200 and 400 μm.

According to a third aspect of the complete mixed feed for fish larvae, the granule size ranges between 120 and 200 μm.

Finally, according to a fourth aspect of the complete mixed feed for fish larvae according to the invention, the granule size is lower than 120 μm.

The complete mixed feed for fish larvae above-described exhibit nutritional qualities, whereby it is adapted to be widely used, i.e. both to feed fresh water fishes and sea fishes.

Preferably, the complete mixed feed for fish larvae according to the invention is intended to feeding sea water fishes of any origin. It is indeed not only adapted to feeding European fishes, such as basses, giltheads or turbots, but also to feeding farmed exotic fishes, such as lates or also umbra.

The complete mixed feed for fish larvae according to the invention has such qualities that it offers both survival and growth rates of larvae never reached up to now as well as the production of larvae exhibiting a particularly low morphological malformation rate and an exceptional maturity degree, compared to the feed substitutes described in the state of the art.

The invention additionally aims at offering a method for preparing a complete mixed feed for fish larvae, said method being characterized in that it comprises the following steps of:
  a) obtaining a paste, mixing water and at least three raw materials in the following proportions:
    (i) fish meal in a proportion ranging from 50 to 65% by weight of the final blend;
    (ii) fish soluble protein concentrate in a proportion ranging from 8 to 25% by weight of the final blend;
    (iii) soya lecithin in a proportion ranging from 7 to 25% by weight of the final blend;
  b) granulating, by wet route, the paste thus obtained in the form of filaments;
  c) deep-freezing the paste filaments at a low temperature, preferably at a temperature lower than −80° C.;
  d) crushing and/or grinding the filaments of the paste deep-frozen paste in step c);
  e) sieving the granules obtained in the crushing step.

The grinding or crushing step of the extruded filaments is particularly facilitated because of the preliminary deep-freezing step. Indeed, the initial paste resulting from the blend of water added to raw materials has an important lipid concentration, resulting in plugging the grinding devices and the sieves used to produce feed particles.

In contrast, the preliminary deep-freezing step makes it possible to offer the initial composition in a solid and crumbly form, particularly adapted for the crushing and then sieving steps.

The method according to the invention is moreover characterized in that water is added at the initial blend point of step a), in a quantity ranging from 10 to 15% of the blend weight. The function of this particular step is to make it possible to bind the particles of the various raw material components in order to obtain a homogeneous paste at the end of the blending initial step.

The method according to the invention additionally advantageously comprises a drying step of the paste filaments obtained after the granulating step b) in order to adjust the water content of the filament composition at a value lower than 14%, preferably at a value ranging from 7 to 10%, and most preferably at a value of about 8%.

The drying step could advantageously be performed at a temperature of 50° C. for 20 minutes.

The drying step is carried out before the deep-freezing step; it is preferably carried out further to the granulating step b) by wet route.

The invention also relates to a breeding method for fish larvae, characterized in that the larvae are fed in an amount ranging from 1 to 4 g/day and per 2500 larvae, using the complete feed above-described.

The invention will be moreover illustrated, without consequently being limited, by the following figures and examples.

DETAILED DESCRIPTION OF THE FIGURES

FIG. 1: Growth of bass larvaes fed with living prey or with feed substitutes

On ordinates: larvae weight expressed in mg of wet material.

On abscissas: larvae age expressed in the number of days after hatching.

The growth has been observed from day 9 until day 40 after hatching for larvae fed from day 9 until day 40 exclusively with living prey (Artemia), with a complete feed composition according to the invention or with the H19 composition of the state of the art (CAHU et al., 1999). Each dot represents the result of the mean±standard deviation of 4 lots of 10 larvae.

Figure 2:
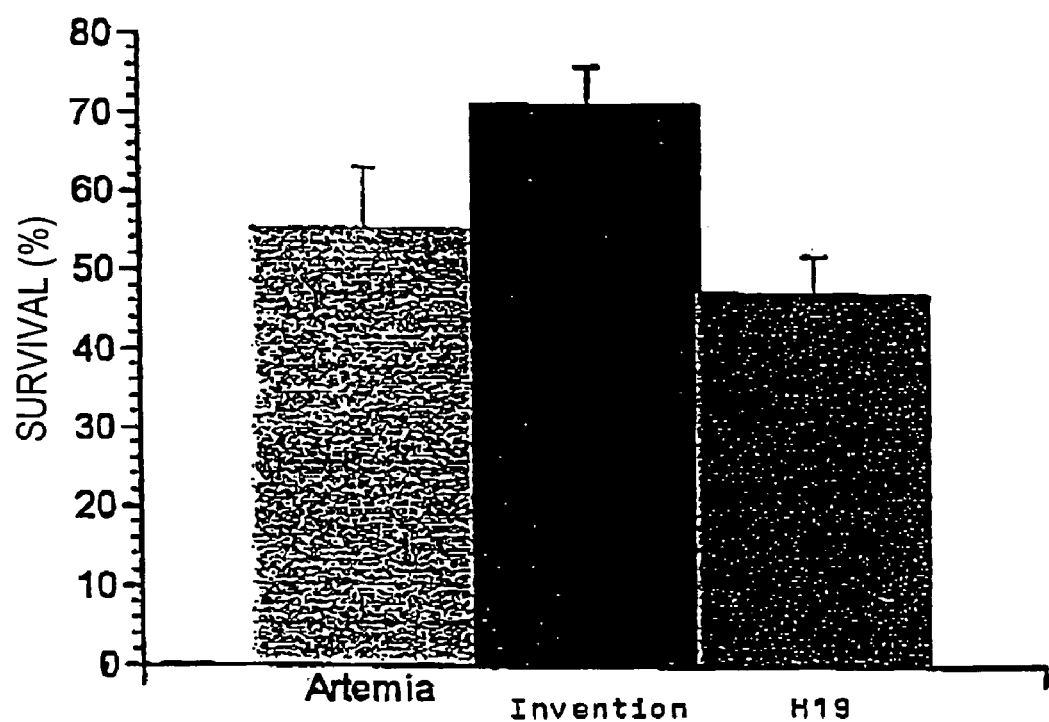

FIG. 2: Study of the larvae survival at day 40

On the ordinates: larvae survival rate expressed in percentages of living larvae, calculated by the ratio of living larvae at day 40 to the number of living larvae at day 2 after hatching.

The survival percentage has been determined for larvae exclusively fed with living prey (Artemia), a feed substitute of the state of the art H19 and the complete feed composition according to the invention. Each dot represents the result of the mean+/−standard deviation of 4 lots.

EXAMPLES

Example 1

Preparation of a complete mixed feed for fishes according to the invention

In a first stage, the raw materials being used and more particularly fish meal, are sieved before being blended, so as to obtain particles of each of the raw materials having a size lower than 160 μm.

The raw materials are as follows:
  the fish meal is the meal sold under the name NORSE™ LT94, having a protein content higher than 78% by weight of the dry matter and sold by NORSILDMEL company,
  the fish soluble protein concentrate (fish protein hydrolysate) is the CPSP™ special G, sold by SOPROPECHE company, the soya lecithin, referred to as D10, is sold by the SAPA-DAFA company, the betaine has the hydrochloride form having a purity higher than 99% and is sold under the reference B3501 by the Sigma company, the vitamin blend used is sold under the reference 762 by the UPAE-INRA company, the mineral blend used is sold under the reference 763 by the UPAE-INRA company.

The above-mentioned raw materials have been mixed in a steel bowl driven by a mechanical arm, after adding 10% of water (by weight of the initial blend) in order to obtain the particle binding of the various components.

The homogeneous blend of raw materials then goes through a spinneret in order to form 3 mm diameter long cylindrical filaments ("spaghetti").

The raw material filaments are subsequently dried in order to bring the water content to about 8% by weight of the final blend. The drying step is carried out in a hot air flow drying-room at 50° C. for 20 minutes.

The 3 mm diameter filaments, the water content of which has been adjusted, are then submitted to a liquid nitrogen deep-freezing step for about ten seconds.

The deep-frozen filaments are then submitted to a crushing step in a grinder and are shaped as granules by using known means. Preferably, a low temperature is maintained during this step so as to prevent the grinder from being plugged.

The granules obtained at the preceding step are then deep-frozen in liquid nitrogen and passed through sieves. Successive sieves have been used so as to separate the granules in various fractions, with a size respectively ranging between 400 and 600 µm, 200 and 400 µm, 120 and 200 µm and finally a size lower than 120 µm.

The thus obtained granules have a water content of 8% of the dry matter. The precise formulation of the complete feed composition is as follows:

| Ingredients | % of dry matter |
| --- | --- |
| Fish meal | 56 |
| Fish soluble protein concentrate | 14 |
| Soya lecithin | 17 |
| Vitamin mixture | 8 |
| Mineral mixture | 4 |
| Betaine | 1 |

The granule composition, expressed with respect to the feed dry matter is as follows:

| | |
| --- | --- |
| total proteins (N × 6.25): | 56%, |
| total phospholipids: | 12%, |
| total lipids: | 26%, |
| ashes: | 14%., |

Example 2

Survival and Growth of Bass Larvae Fed with the Complete Mixed Feed According to the Invention and Comparison with a Feed Substitute Representative of the State of the Art for Larvae Aged from 9 to 40 Days Bass larvae (*Dicentrarchus labrax*) have been distributed in 35 l pools in an amount of 60 larvae/l. The larvae have been fed using Rotifera (*Brachionus plicatilis*) for a time period of 3 days after the mouth opening.

The larvae have then been divided into two groups of four lots and the larvae survival and growth have been observed from day 9 until day 40 after hatching (i.e. from day 4 until day 35 after the mouth opening).

The first group of four lots has exclusively been fed with *Artemia nauplii*. The second group of four lots has exclusively been fed using the complete mixed feed of the invention, according to example 1.

The remaining breeding conditions have been standardized in the pools, the water temperature being maintained at 20° C., with a 35 ppm salinity. The pools are permanently lit.

The larvae feeding has been performed using automatic dispensers of running belt type secured above the pools and the feed has been delivered permanently to the larvae (24/24).

The complete mixed feed daily quantities are 1 g/day per 2500 larvae at the beginning of the feeding cycle and have been progressively increased up to 4 g/day per 2500 larvae at the end of the feeding cycle (day 40 after hatching).

The feed quantities used correspond to an excess distribution affording a permanent availability of the granules or the living prey for the larvae.

According to the selected feed distribution method, the complete mixed feed slowly settles in the column, making impossible for the larvae to grab the granules during this slow settling step.

Every day, the excess feed and faeces deposits being accumulated at the bottom of the pools are removed with no putting in suspension again.

After feeding during 32 days (40 days after hatching), the results, expressed as the mean+/−standard deviation, are as follows:

| | Complete feed | Artemia | H19 |
| --- | --- | --- | --- |
| Survival (%) | 70 +/− 6.9 | 55 +/− 8.1 | 47 +/− 6.2 |
| Average weight (mg) | 32 +/− 3.8 | 35 +/− 4.1 | 6 +/− 0.8 |

The results obtained under the same breeding conditions using the H19 feed substitute representative of the state of the art (CAHU et al., 1999) are also given by way of comparison.

The indicated survival corresponds to the larvae number at the end of the experiment ($40^{th}$ day after hatching) expressed in percentage of the initial number of larvae bred two days after hatching (FIG. 2).

The individual mean weight has been calculated as from four 10 larvae takings for each pool of a same experimental lot.

The larvae growth has been observed from day 9 until day 40 after hatching and the experimental results are represented in FIG. 1.

The results of FIG. 1 show that the effects of the complete mixed feed according to the invention on the larvae growth are quite comparable, and even identical, to the properties of the *Artemia nauplii*.

At day 40 after hatching, the larvae fed with the complete mixed feed according to the invention have a weight (32 mg) which does not significantly differ from the weight of the larvae fed with the *Artemia* (35 mg).

On the other hand, the larvae fed using the H19 feed substitute of the state of the art have an extremely low growth rate, as the weight of the larvae fed with this substitute at day 40 is about 5 mg, i.e. a weight six times lower than that obtained using the complete mixed feed according to the invention.

60 days after hatching, the larvae that have never received any *Artemia* weighed 300 mg on average and exhibited an harmonious development, more particularly at the skeleton level.

The table results indicate a significantly higher survival with the larvae having received the complete mixed feed according to the invention than the larvae fed with the *Artemia* or the H19 feed substitute.

These results clearly show that the complete mixed feed according to the invention advantageously replaces the *Artemia* in the breeding sequence of the bass larvae and that this feed substitute even affords a survival rate of the larvae significantly higher than the survival rate obtained using a larvae feeding based on living prey.

Example 3

Survival and Growth of Bass Larvae Fed with the Complete Mixed Feed According to the Invention for Larvae Aged from 5 to 10 Days The breeding general conditions of the bass larvae are those presented in example 2. After the mouth opening, i.e. 5 days after hatching, the larvae are divided into two groups, the first group of 4 lots has been exclusively fed with Rotifera, whereas the second group of 4 lots has been fed with the complete mixed feed according to the invention. The feed particles have a size lower than 120 μm.

After 5 day feeding, the average weights are 0.85+/−0.07 mg for the larvae fed with the mixed feed according to the invention, whereas it only reaches 0.76+/−0.10 mg for the larvae fed with the Rotifera. The survival was identical in both groups (92%).

This example shows that the complete feed according to the invention advantageously replaces the Rotifera and can be used as a sole feed during the whole breeding stage of the fish larvae.

This feed exhibits an interest for species the larvae breeding of which uses a long use of Rotifera, such as turbot or gilthead.

Example 4

Comparative Study of the Quality and Maturity of the Bass Larvae Fed with the Complete Mixed Feed According to the Invention or the H19Feed Substitute Physiological parameters have been measured in larvae from the experiments described in example 2.

At the 40$^{th}$ development day, only 3.8+/−1.5% of the larvae fed with the complete mixed feed according to the invention show a skeleton malformation. This rate was 6+/−1.2% with the larvae fed with the feed substitute, called H19 in the article by CAHU et al. 1999.

The maturity degree of the digestive functions has been evaluated using two parameters: the secretion of a pancreatic enzyme and the occurrence, in the enterocyte brush-forming edges, of an enzyme typical of the digestion of the adult type, the alkaline phosphatase.

The larvae fed with the feed according to the invention exhibited a trypsine secretion rate of 55+/−5.5%, higher than that of the larvae fed with the feed substitute, called H19 43+/−4.9%.

The alkaline phosphatase activity reached 308+/−10.7 mU/mg of proteins in the larvae fed with the H19 feed substitute.

The use of the feed according to the invention is advantageous for producing larvae having a good morphological and physiological quality. More particularly, the digestive function maturity during the larval life is indispensable for a good subsequent fish development.

The invention claimed is:

1. A complete feed composition for fish larvae, comprising:
   i) a phospholipid content ranging from 10 to 20% by weight of the dry matter of said feed;
   ii) non-hydrolyzed protein ranging between 45 and 60% by weight of the dry matter of said feed; and
   iii) hydrolyzed proteins ranging between 10 and 22% of the dry matter feed.

2. The composition according to claim 1, wherein said composition has a phospholipid content from vegetal origin at least equal to 6% of the feed dry matter.

3. The composition according to claim 1, wherein said composition has a total lipid content higher than 25% by weight of the dry matter.

4. The composition according to claim 1, wherein said composition additionally comprises a vitamin additive blend.

5. The composition according to claim 1, wherein said composition additionally comprises a mineral additive blend.

6. The composition according to claim 5, comprising a content of 14% of hydrolyzed proteins by weight dry matter.

7. The composition according to claim 1, wherein said composition additionally comprises an appetizing factor.

8. The composition according to claim 1, wherein said composition comprises a water content lower than 14% by weight of the final composition.

9. The composition according to claim 1, wherein said composition has the following:

| Ingredients | % of dry matter |
|---|---|
| Fish meal | 56 |
| Fish soluable protein concentrate | 14 |
| Soya lecithin | 17 |
| Vitamin blend | 8 |
| Mineral blend | 4 |
| Betaine | 1. |

10. The feed composition according to claim 1, comprising a content of 14% of hydrolyzed proteins by weight dry matter.

11. The composition according to claim 1, wherein vegetal lecithin is present and accounts for more than 50% of said phospholipids present in said feed.

12. A complete mixed feed for fish larvae made of granules having a composition according to claim 1.

13. The feed according to claim 12, wherein the granule size is lower than 660 μm.

14. A method for preparing a complete feed according to claim 12, comprising the following steps of:
   a) obtaining a paste by mixing water and at least three raw materials in the following proportions:
      (i) fish meal in proportion ranging from 50 to 60% by weight of the final blend;
      (ii) fish soluble protein concentrate in a proportion ranging form 10 to 22% by weight of the final blend;
      (iii) soya lecithin in a proportion ranging from 7 to 25% by weight of the final blend;

b) granulating, by wet route, the paste thus obtained in the form of filaments;
c) deep-freezing the paste filaments at a low temperature, preferably at a temperature lower than −80° C.;
d) crushing and/or grinding the paste filaments deep-frozen at step c);
e) sieving the granules obtained in the crushing step.

15. The method according to claim 14, wherein the water is added, upon the blending step a), in an amount ranging from 10 to 15% by weight of the blend.

16. A feed composition for fish larvae, comprising:
a phospholipid content ranging from 10 to 20% by weight dry matter of said feed,
a total lipid content is higher than 25% by weight of dry matter, a fish meal content ranging between 50 and 65% by weight of dry matter, and
hydrolyzed proteins ranges from 10 to 22% of dry matter.

17. The feed composition according to claim 16, comprising a content of 14% of hydrolyzed proteins by weight dry matter.

18. The feed composition according to claim 16, wherein vegetal lecithin is present and accounts for more than 50% of said phospholipids present in said feed.

19. A complete feed composition for fish larvae, comprising:
i) a phospholipid content ranging from 10 to 20% by weight dry matter of said feed,
ii) a protein content comprising
non-hydrolyzed protein comprising fish meal between 45 and 60% by weight of the dry matter of said feed composition, and
hydrolyzed proteins ranging between 10 and 22% by weight dry matter of said feed composition, and
iii) a final water content not higher than 14%, and
iv) a total lipid content higher than 25% by weight dry matter of said feed; and
wherein the feed composition is in the form of granules smaller than 600 μm in size.

20. The feed composition according to claim 19, wherein vegetal lecithin is present and accounts for more than 50% of said phospholipids present in said feed.

* * * * *